US009551654B2

(12) United States Patent
Ismail et al.

(10) Patent No.: US 9,551,654 B2
(45) Date of Patent: Jan. 24, 2017

(54) METHOD FOR THE SPECTRAL IDENTIFICATION OF MICROORGANISMS

(75) Inventors: Ashraf Ismail, Montreal (CA); Jonah Prevost Kirkwood, Westmount (CA); Jacqueline Sedman, Kirkland (CA); Andrew Ghetler, Montreal (CA); Tom Pinchuk, Charlotte, NC (US); John Austin, Ottawa (CA); Lorraine Gour, Longueuil (CA)

(73) Assignees: MCGILL UNIVERSITY, Montreal (CA); HEALTH CANADA, Ottawa (CA)

( * ) Notice: Subject to any disclaimer, the term of this patent is extended or adjusted under 35 U.S.C. 154(b) by 3243 days.

(21) Appl. No.: 11/630,856

(22) PCT Filed: Jun. 30, 2005

(86) PCT No.: PCT/CA2005/001037
§ 371 (c)(1),
(2), (4) Date: Jan. 17, 2008

(87) PCT Pub. No.: WO2006/002537
PCT Pub. Date: Jan. 12, 2006

(65) Prior Publication Data
US 2008/0132418 A1 Jun. 5, 2008

Related U.S. Application Data

(60) Provisional application No. 60/584,165, filed on Jul. 1, 2004.

(51) Int. Cl.
*G01N 33/48* (2006.01)
*G01N 33/50* (2006.01)
(Continued)

(52) U.S. Cl.
CPC .......... *G01N 21/3563* (2013.01); *G06F 19/12* (2013.01); *G06F 19/18* (2013.01); *G01N 2021/1748* (2013.01); *G01N 2021/1772* (2013.01); *G01N 2021/3595* (2013.01); *G01N 2201/129* (2013.01)

(58) Field of Classification Search
None
See application file for complete search history.

(56) References Cited

U.S. PATENT DOCUMENTS 5,784,162 A * 7/1998 Cabib et al. .................. 356/456

FOREIGN PATENT DOCUMENTS

EP 1491876 A1 12/2004
WO WO2006002537 5/2006

OTHER PUBLICATIONS

Mariey et al. (Vibrational Spectrscopy, vol. 26, p. 151-159, 2001).*
(Continued)

*Primary Examiner* — Russell S Negin

(57) ABSTRACT

A rapid method for characterizing and identifying microorganisms using Focal-Plane Array (FPA)-Fourier Transform Infrared (FTIR) spectroscopy is disclosed. Multi-pixels spectral images of unknown microorganisms spectra are analyzed and compared to spectra of reference microorganisms in databases. The method allows rapid and highly reliable identification of unknown microorganisms for the purpose of medical diagnosis, food and environmental control.

18 Claims, 13 Drawing Sheets

(51) Int. Cl.
*G01N 21/3563* (2014.01)
*G06F 19/18* (2011.01)
*G06F 19/12* (2011.01)
*G01N 21/17* (2006.01)
*G01N 21/35* (2014.01)

(56) References Cited

OTHER PUBLICATIONS

Ngo-Thi et al. (Journal of Molecular Structure, vol. 661-662, p. 371-380, 2003).*

Kummerle, et al., "Rapid and Reliable Identification of Food-Borne Yeasts by Fourier-Transform Infrared Spectroscopy", Applied and Environmental Microbiology, Jun. 1998, vol. 64, No. 6, pp. 2207-2214.

Lewis, et al., "Fourier Transform Spectroscopic Imaging Using an Infrared Focal-plane Array Detector", Analytical Chemistry, Oct. 1, 1995, vol. 67, No. 19, pp. 3377-3381.

Beattie, et al., "Discrimination Among *Bacillus cereus, B. mycoides* and *B. thuringiensis* and Some Other Species of the Genus *Bacillus* by Fourier Transform Infrared Spectroscopy", Fems Microbiology Letters, Jul. 1, 1998, vol. 164, No. 1, pp. 201-206.

Rodriguez-Saona, et al., "Rapid Detection and Identification of Bacterial Strains by Fourier Transform Near-Infrared Spectroscopy", Journal of Agricultural and Food Chemistry, Feb. 2001, vol. 49, No. 2, pp. 574-579.

Al-Khaldi, et al., "Accelerating Bacterial Identification by Infrared Spectroscopy by Employing Microarray Deposition of Microorganisms", Foodborne Pathogens and Disease, 2004 Fall, vol. 1, No. 3, pp. 172-177.

Kirkwood, et al., "Fourier Transform Infrared Bacteria Identification with the Use of a Focal-Plane-Array Detector and Microarray Printing", Applied Spectroscopy, Nov. 2004, vol. 58, No. 11, pp. 1364-1368.

PCT/CA2005/001037, International Search Report, mailed Oct. 19, 2005, relevant pp. 4 and 5.

Wenning, et al. "Fourier-transform infrared microspectroscopy, a novel and rapid tool for identification of yeasts" Applied and Environmental Microbiology, Oct. 2002, p. 4717-4721.

* cited by examiner

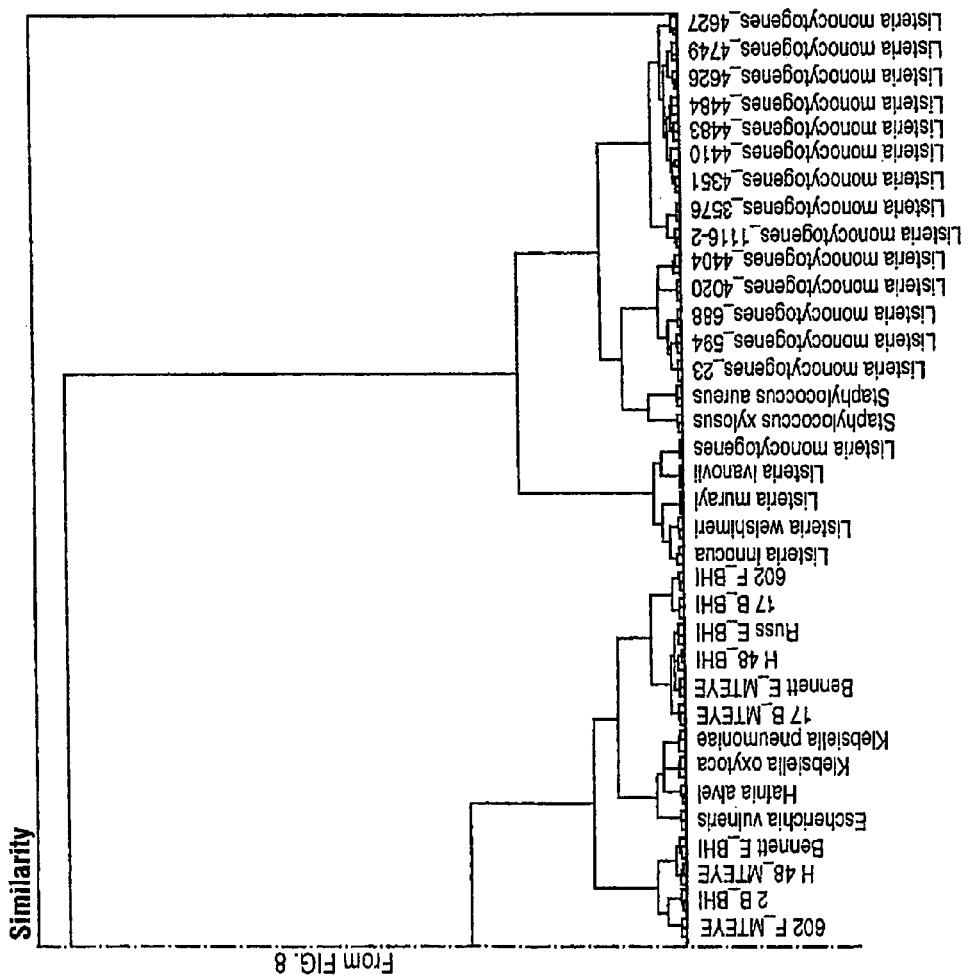

METHOD FOR THE SPECTRAL IDENTIFICATION OF MICROORGANISMS

FIELD OF THE INVENTION

The present invention relates to methods of microorganisms identification using spectral data.

BACKGROUND OF THE INVENTION

Fourier transform infrared (FTIR) spectroscopy is a known technique for the identification of microorganisms (Mariey et al., 2001 Vibr. Spectrosc. 26:151). Infrared (IR) spectroscopy measures the vibrations of chemical bonds within all the biochemical constituents of cells, i.e., proteins, lipids, polysaccharides, and nucleic acids, and provides quantitative information about the total biochemical composition of the intact whole microorganism. Furthermore, because the IR spectra of microorganisms consist of distinct and unique patterns the spectra effectively serve as "fingerprints," allowing for their use in taxonomic discrimination. Indeed, the use of IR spectroscopy as a means of differentiating and identifying bacteria was extensively reported as early as the 1950s. However, it was concluded at that time that, although individual strains of bacteria definitely exhibit unique IR spectra, the identification of bacteria by IR spectroscopy could not be regarded as a useful technique, as the procedure was too time-consuming and impractical. Indeed, reports on the study of microorganisms by IR spectroscopy became less frequent in the 1960s and virtually ended in the mid-1970s.

Interest in this technique revived in the early 1990s, when the development of FTIR spectroscopy in combination with the emergence of chemometric techniques for the analysis of FTIR data opened a wide range of new applications for IR spectroscopy (Griffiths and Chalmers eds, 2001 Handbook of vibrational spectroscopy, John Wiley & sons, New-York, vol. 5). Beginning with the pioneering work by Naumann and co-workers in Germany (Naumann et al., 1991 Nature, 351:81; Helm et al., 1991 J. Gen. Microbiol. 137:69), FTIR spectroscopy has been demonstrated within the past decade to be useful for microbial analysis (Naumann, 2000 infrared spectroscopy in microbiology, in: R. A. Meyers (eds) encyclopedia of analytical chemistry, Wiley, Chichester pp. 102-131). The method is uniformly applicable to virtually all microorganisms that can be grown in culture.

Suggested potential microbiological applications of FTIR spectroscopy include (i) identification of life-threatening pathogens in the clinical laboratory: (ii) epidemiological investigations, conductance of case studies, screening of pathogens, hygiene control, elucidation of infection chains, therapy control, and detection of recurrent infections; (iii) characterization and screening of microorganisms from the environment; (iv) monitoring of biotechnological processes; (v) microbiological quality control in the food and pharmaceutical industries; and (vi) maintenance of strain collections.

The fundamental requirement for FTIR identification of microorganisms is that the variance within the spectra of one taxon must be smaller than the variance among spectra of different taxa. Although the variations in biochemical composition among different taxa do result in differences in their IR spectra, these differences may be very slight (e.g., between different strains). Thus, the above requirement imposes stringent conditions on spectral reproducibility, and interest in IR bacteria identification waned in the 1960s largely because these conditions could not be achieved with the IR instrumentation available at the time The reproducibility of the sample-handling technique employed to acquire the FTIR spectra of bacteria is also of critical importance. Analysis of IR spectra to determine identification of microorganisms by providing a fingerprint has been used in the past. However, such analyses have yielded relatively poor reproducibility and identification success rate. FTIR spectra of bacteria are normally recorded by depositing cells suspended in saline solution on an optical window (e.g., ZnSe) and drying the sample to form a bacterial film. Spectral variability results from differences in the distribution of the cells on the IR window, thickness of bacterial film, moisture content of the film and the like.

FTIR spectra of microorganisms are commonly acquired in the transmission mode, although various other techniques such as attenuated total reflectance (ATR) and diffuse reflectance spectroscopy (DRIFT) have also been employed. For spectra acquired in the transmission mode, spectral reproducibility depends mainly on the uniformity of the sample (sample homogeneity, particle size) and sample thickness (or pathlength). Sample nonuniformity leads to baseline variations owing to the scattering, diffraction, and refraction that occur as the IR beam passes through the sample, whereas variations in sample thickness result in variations in band intensity, although consistency in relative peak intensities is maintained.

Conventional IR methods for bacterial identification have a number of additional drawbacks. For example bacterial cells must be extensively cultured prior to FTIR analysis to increase the overall biomass and then transferred from the growth media onto an IR-transparent optical window, an IR-reflecting substrate, or an IR internal reflection element for spectral collection in the transmission mode, transmission-reflection, or attenuated total reflectance mode, respectively. Both these steps represent bottlenecks that have prevented the speed advantages of FTIR bacteria identification from being fully exploited. Furthermore, they make building a spectral library a laborious and time consuming process, which likely accounts, in part, for the lack of commercial bacterial infrared spectral databases that would be required in order for FTIR bacteria identification to be implemented in routine microbiological analysis.

U.S. Pat. No. 5,660,998 to Naumann and Labischinski describes a method for identifying bacteria by obtaining IR spectra of small colonies. The colonies of between 50 to 4,000 cells are deposited on a surface, localized with a microscope and a spectrum of each colony is obtained. However, when microorganisms are deposited on a surface or suspended in a solution for acquisition of spectral data, there usually results an inhomogeneous distribution of the microorganisms within the sample. Conventional acquisition of spectral data does not discriminate regions of inhomogeneities and therefore provides an "average" signal, which may comprise signal contributions that render the spectral information less reliable for identifying microorganisms. Furthermore, bacterial colonies, even when originating from a pure strain, may exhibit physiological and biochemical variability that can influence the reproducibility of the spectral data.

There is therefore a need for improved methods for identifying microorganisms using spectral data.

SUMMARY OF THE INVENTION

The present invention provides a method for the identification of microorganisms that overcome the limitation of the prior art. In one embodiment there is provided a method for characterizing a microorganism the method comprising obtaining at least one multi-pixels spectral image of the microorganism and selecting one or more spectra from the multi-pixels spectral image based on pre-determined spectral characteristics wherein the selected spectra comprise spectral information characteristics of the microorganism.

In another embodiment the method further provides for the identification of microorganisms by comparing the selected spectra of the microorganism with spectra of reference microorganisms in a database to determine its identity.

In yet another embodiment the method also provides for the establishment of a database by: obtaining at least one multi-pixels spectral image for each of a plurality of reference microorganisms, each pixel exhibiting a signal corresponding to a spectrum of a reference microorganism; and selecting spectra from the multi-pixel spectral images based on pre-determined spectral characteristics to establish the database, wherein the database comprises at least one spectrum for each of the reference microorganisms.

In another aspect of the invention sub-databases are provided comprising partial or transformed spectral data to reduce data space and allow faster analysis of the unknown sample.

The method allows rapid and highly reliable identification of unknown microorganism for the purpose of medical diagnosis, food and environment control and the like.

BRIEF DESCRIPTION OF THE DRAWINGS

Further features and advantages of the present invention will become apparent from the following detailed description, taken in combination with the appended drawings, in which.

DETAILED DESCRIPTION OF THE INVENTION

The present invention relates to methods for identifying microorganisms using multi-pixels spectral data.

In this application by microorganism it is meant any unicellular or multicellular microorganism such as but not limited to bacteria, viruses, unicellular eukaryotes and the like.

The present inventors have discovered a method that enables spectral characterization of microorganisms that essentially eliminates the problems related to sample inhomogeneity. In a broad aspect of the invention there is provided a method for spectrally characterizing microorganisms. Furthermore the method significantly reduces the impact of spectral inhomogeneity of a microorganism sample on the reliability of identification of the microorganism. In one embodiment of the invention, a sample of the microorganism is deposited on a surface and spectral data is acquired from a plurality of regions within the sample with a spatial resolution sufficient to distinguish spectral variations within the sample. In a preferred embodiment the acquisition is performed simultaneously for the plurality of regions using an array detector with the resolution being determined by the array size. It has been found that the reliability of the characterization of the microorganism can be increased significantly by selecting regions generating signals that exhibit predetermined spectral characteristics.

The acquisition of the signals from different regions of a sample is preferably performed by obtaining a multi-pixels spectral image. The image is obtained by illuminating the sample with light at one or more wavelengths and the attenuation signal is detected at a plurality of detection points corresponding to different regions of the sample. In a particular embodiment the attenuation signal is detected using an array detector such as a linear array or multiple array detector such as a camera as for example a CCD camera. In a preferred embodiment the image is recorded using infrared light and in a more preferred embodiment the image is obtained using Focal Plane Array Fourier Transform Infrared Spectroscopy (FPA-FTIR).

Figure 1:
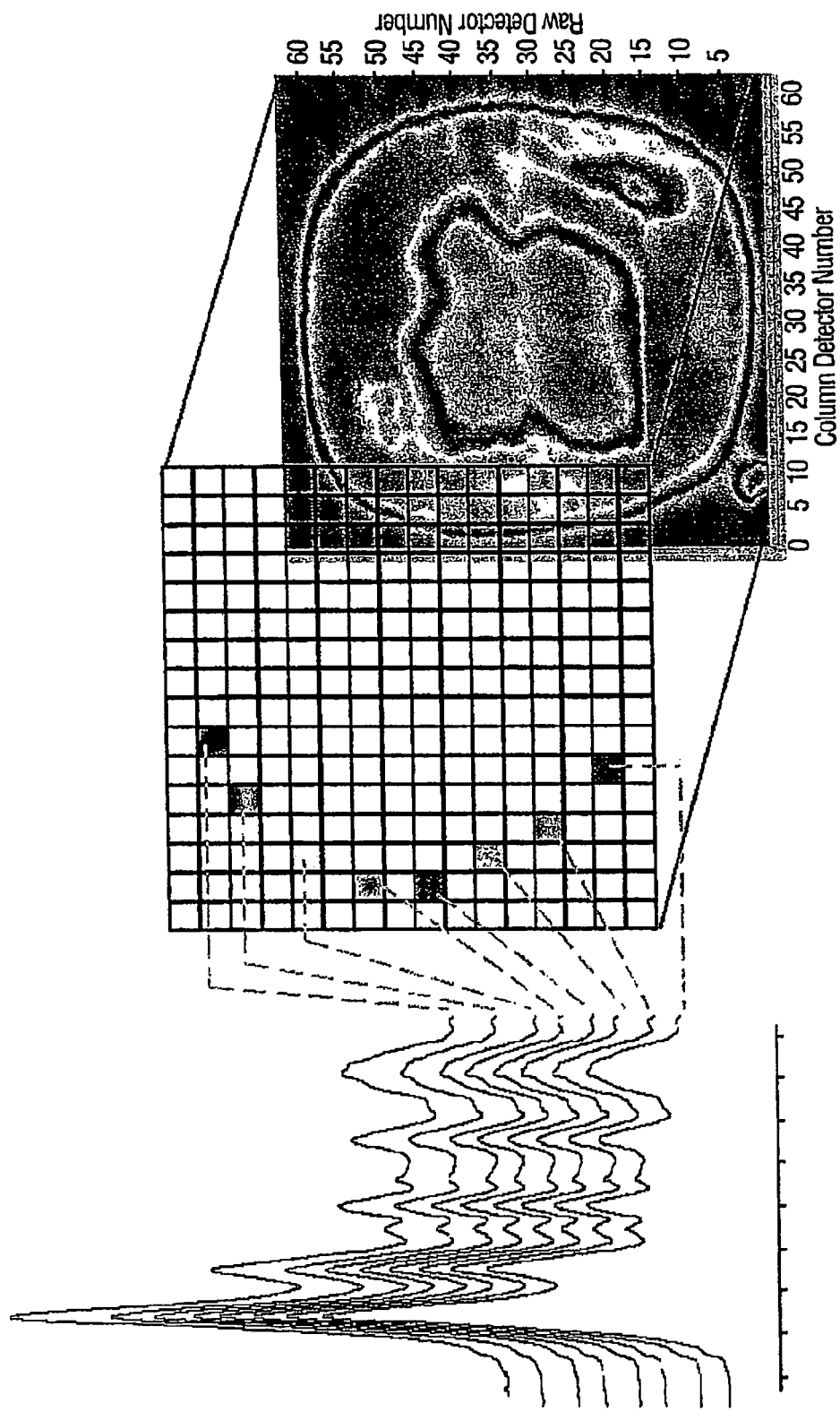
FIG. 1 is an FPA-FTIR image of a bacterial sample also showing the associated pixels and some exemplary spectra.

In FPA-FTIR spectroscopy the sample is deposited on an IR transparent surface such as zinc selenide for example and an IR spectrum is obtained from the signal detected at each pixel of a multi-pixel detector. The deposition of the sample onto the surface is preferably performed automatically but it may also be performed manually. Advantageously, only a very small amount of the microorganism is needed and can be obtained from any suitable source as for example from a colony grown on a suitable medium. The sample is applied onto the surface such as to cover an area preferably no larger than the surface that can be detected by a single array detector. A typical multi-pixels spectral image is shown in FIG. 1 with a schematic representation of the array of pixels and examples of spectra that can be obtained from each pixel.

The deposition of the sample can be done manually or automatically. For example, a toothpick can be used to collect a small sample from a bacterial colony. Alternatively, a microorganism solution can be pipetted onto the surface. Automated techniques known in the art or techniques used to deposit small amount of sample, such as described in U.S. Pat. No. 5,660,998 can also be used for sample deposition. FIG. 1 exemplifies the fact that deposition of a microorganism on a surface, in this case an IR transparent surface, can produce a very heterogeneous spatial distribution of the sample.

Figure 2:
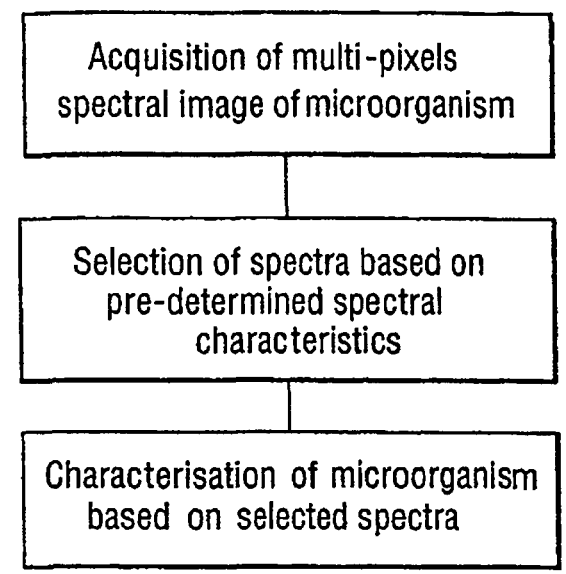
FIG. 2 is a flow chart diagram of the of an embodiment of the method of the invention for the spectral characterization of a microorganism.

After deposition of the sample on the surface and with reference to FIG. 2, data is acquired, preferably using an FPA-FTIR spectrometer to record a multi-pixels image with each pixel generating a spectrum of a region of the sample. In a second step, spectra are selected to retain only those spectra that exhibit predetermined spectral characteristics such as to provide a spectral characterization of the microorganism. The pre-determined spectral characteristics on which the selection of spectra (corresponding to given pixels) is based are those that influence the quality of the spectrum. For example, the selection may be based on signal to noise ratio, spectral intensity at one or more specific wavelengths, quality of the baseline and the like. While absolute values of the pre-determined spectral characteristics can serve to determine whether a spectrum is retained, the selection may also be based on the relative deviation from the characteristics of a reference spectrum.

Figure 3:
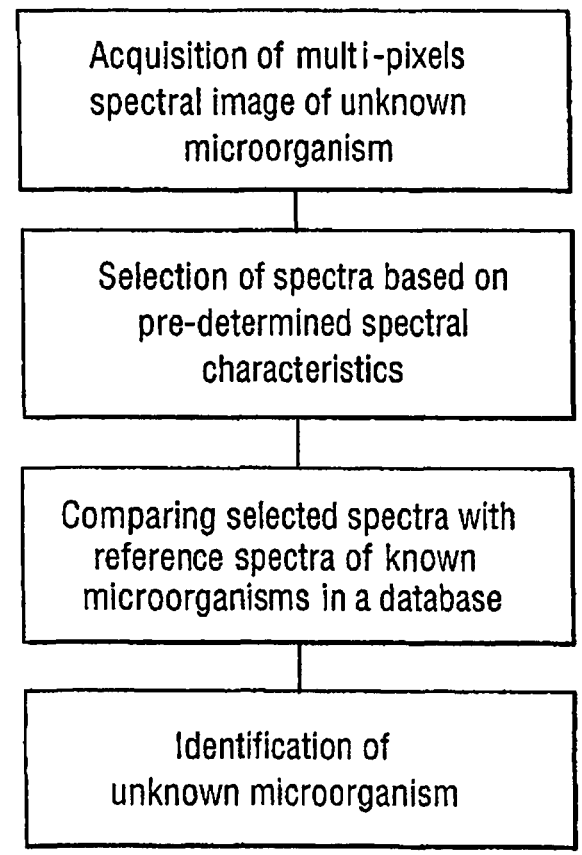
FIG. 3 is a flow chart diagram of the of an embodiment of the method of the invention for the spectralidentification of a microorganism.
Figure 4:
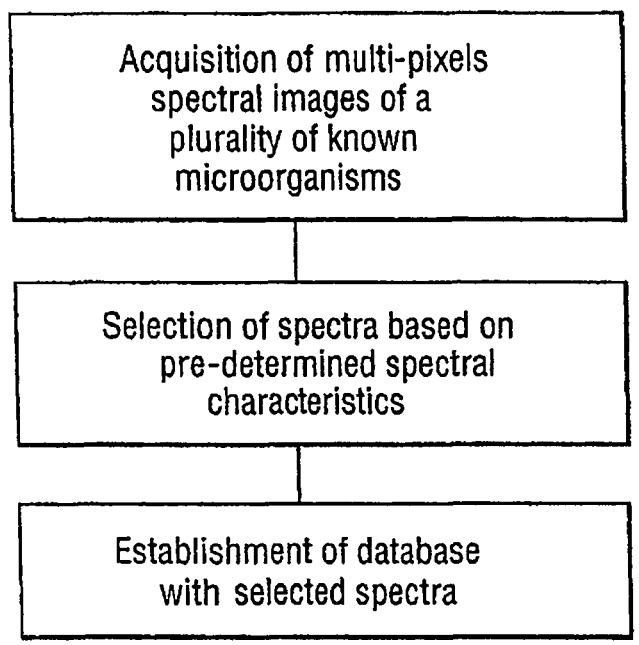
FIG. 4 is a flow chart diagram of the of an embodiment of the method of the invention for the establishment of a database using reference microorganisms.

The characterization of the sample may comprise the identification of a microorganism by comparing one or more of the selected spectra with spectra of reference microorganisms stored in a database (FIG. 3). While the database may consist of spectra acquired using known methods, it preferably comprises spectra of reference microorganisms obtained using the method of the present invention (FIG. 4). That is to say, the database is built by acquiring images of known (reference) microorganisms and selecting spectra from pixels of these images exhibiting desired pre-determined spectral characteristics. For each reference sample, a large number of spectra can be acquired with one multi-pixels image.

Optionally, the selected spectra may be processed to facilitate the characterization, or identification of the microorganism. The processing may involve but is not limited to: obtaining a derivative of the spectrum, deconvolution, baseline correction, normalizing of peak height or peak area and the like.

Because of its high spatial resolution, the method of the invention also advantageously provides for the characterization of samples and the establishment of databases that reflects chemical inhomogeneities. By chemical inhomogeneities it is meant chemical variations within a sample that are reflected in the spectra. The chemical variations may occur as result of the presence of a mixture of microorganisms or the presence of chemical "contaminant" species or chemical species secreted by the microorganisms. In this respect, a microorganism sample may exhibit biochemical/molecular variations, which may be intrinsic to the microorganism. Such chemical inhomogeneities may arise, for example, from the synthesis of certain molecules at certain phases of colony growth or under certain growth conditions. These chemical inhomogeneities may be present or not in the samples used to establish the database and, similarly, they may or may not be present in the unknown samples. With the method of the present invention it is possible to identify spectra comprising (or not) chemical inhomogeneities and, if they are present. Depending on the needs, chemical inhomogeneities may be included or excluded from the analysis. That is to say, chemical inhomogeneities may be exploited to identify a plurality of organisms simultaneously or to provide additional spectral features to help characterize or identify a particular microorganism. The method of the invention therefore avoids the need of using complex and tedious purification protocols to eliminate such chemical inhomogeneities.

Thus in addition to improving spectral characterization and identification of microorganisms by eliminating signal contributions that may distort the spectrum, the method of the invention can also exploit the chemical inhomogeneities of a sample to take advantage of intrinsic sample variations that are reflected in the spectra from the different regions of the sample and thereby provide additional spectral information for characterization and identification of microorganisms.

In a further embodiment, sub-databases can be generated that comprise partial or transformed spectral data obtained from the selected or processed selected spectra to reduce dimensionality of the data space and reduce the time required to analyze the data. Examples of methods of data space reduction include but are not limited to: (i) principal component analysis and (ii) application of region selection algorithms directly to the spectral data to identify the most relevant spectral information for differentiation of the bacteria in the database. The comparison of an unknown sample with reference samples can therefore be performed using at least one sub-database or a combination of one or more sub-database or a database comprising complete spectra.

The signal-to-noise ratio (SNR) of a spectrum obtained from a signal recorded at a single pixel of a FPA detector was found to be adequate for reliable microorganism identification. However, it will be appreciated that multiple spectra can be co-added to produce a spectrum having a higher SNR. Furthermore, in the embodiment in which an unknown microorganism is being identified, individual spectra or subsets of spectra from the image of the sample to be identified can be compared with spectra of reference microorganisms in the database. By comparing different subsets of spectra with reference spectra it is possible to establish a confidence level for the accuracy of the comparison.

Advantageously multiple samples can be analyzed simultaneously, using the method of the invention, from a single FPA-FTIR image. In this respect several samples can be deposited on an IR transparent surface such that the samples will be simultaneously included in the IR beam diameter. While the samples should preferably be separated to avoid spatial overlapping, the spatial discrimination power of the method can be exploited to obtained spectra from each individual sample even if there is partial overlap. The method therefore provides for a high throughput allowing rapid identification of multiple samples. Furthermore, because of the small number of cells required, the time required for growing the samples is considerably reduced compared with other techniques which require greater sample quantities.

Algorithms for matching the spectra of unknown samples, such as organic chemicals for example, with reference spectra in databases are known in the art. These algorithms can be used for matching the spectra of bacteria. For example, K-nearest-neighbor algorithm, artificial neural networks, multivariate statistics, support vector machines and hierarchical database distribution and combination thereof can be used for bacteria identification by spectral matching against a database.

Furthermore methods for minimizing search times are also known in the art and can be applied to the present method. In one embodiment, hierarchical database distribution is used to minimize search times and allows the spectrum of an unknown to be matched against a database of over 300,000 spectra in a matter of seconds. For example, the identification of an unknown bacterium can start by first identifying whether it is Gram positive or a Gram negative. This can be achieved by comparing spectral regions having features that distinguish the two types of organisms (for example spectral bands corresponding to outer membrane components). Then the genus is identified, followed by identification of the species and finally the strain. At each step a subset of spectra (from a sub-database for example) is used to minimize search time.

EXAMPLES

Example 1

In this experiment 80 bacterial samples were characterized by FPA-FTIR. All spectra were collected on a Digilab FastIR imaging spectrometer equipped with a Digilab UMA-600 infrared microscope and a 16×16 MCT focal plane array detector (Digilab, Randolph, Mass., USA) operating under Win-IR Pro 3.3 (Digilab) by co-adding 256 scans at a resolution of 8 cm$^{-1}$. In order to produce an absorbance, all single beam spectra and focal plane array imaging spectra were ratioed against the open beam spectrum of the sample. A constant flow of dry air was employed to purge the spectrometer and the microscope of carbon dioxide and water vapor. In total, (for the 80 bacterial samples) over 200,000 spectra of bacteria and bacterial cell extracts were recorded from the spectral images, yielding an average of 250 good pixels out of a possible 256 pixels per image, (each pixel generates a unique spectrum). A sterile wood toothpick was inserted into isolated colonies of bacteria to gently scrape some from the growth plate. The bacteria were then deposited onto the surface of a ZnSe crystal in an area of one millimeter square. In order to prevent cross contamination of the bacterial spots on the zinc selenide crystal the spots were overlaid onto a grid with a 1-millimeter area, and empty wells were always left between bacterial samples on the crystal. The bacteria were air dried on the support for 10 minutes, and irradiated with ultraviolet light for a subsequent 10 minutes to ensure bacterial cell fixation.

The high degree of spectral similarity of bacterial species within the same genus and the fact that each of the eighty samples analyzed have thousands of absorbance measurements for each sample, necessitates computerized methods of classification. The primary method of bacterial classification was done through the use of hierarchal cluster analysis (HCA) using a commercial software (MINITAB™). The preferred method of bacterial identification in this study was an unsupervised method of classification that relied on selected combinations of spectral regions of the infrared spectrum. Multivariate statistical analysis considers numerous properties of the spectra at the same time, whereas univariate statistical analysis only evaluates a single parameter of the object (i.e. a single absorbance value at a determined wavenumber). Multivariate analysis techniques allow for the investigation, treatment, and graphical illustration of complex data configurations in the form of hierarchical graphs known as dendrograms. Prior to multivariate analysis the raw data from the spectra were normalized (e.g. by peak height or area), and subsequently filtered (e.g. by taking the first or second derivative). Furthermore, the spectral ranges of interest were pre-selected to allow for proper hierarchical clustering.

Hierarchical cluster analysis can be used to group data sets relative to their intrinsic similarities. This method can be used when the groups of spectra are initially unknown and when there is no outside information about grouping. Applied to bacterial identification by FTIR, there are numerous regions of the MID-IR spectrum that can be used to create different dendrograms (graphical representations of the hierarchical clusters), therefore the choice of final grouping is usually data specific, and is determined after viewing clustering statistics. As such, regions of the IR spectra (or the entire spectrum as the case may be) are selected to ensure that the dendrograms created will reflect the parameter under study. The principle of cluster observations is a method that creates an agglomerative hierarchic graph that begins with all observations being separate, each forming its own cluster. The MINITAB™ software begins processing the data by joining the two observations (or spectral regions in this instance) that are the most similar to each other. Spectra of the same species will be expected to have spectra that most resemble each other, as an infrared spectrum is a representation of the entire biochemical composition of the bacterial sample. Therefore, by controlling the growth media and sample deposition hierarchical clustering can join two spectra from the same strain together in the first step. Subsequently, either a third observation joins the first two (if it is a spectrum from the same species as above), or the first step is repeated to join two other observations together into a second cluster (a second species). The agglomeration process will continue until all the similar spectral regions are clustered into one. If the samples are from different strains and have unique infrared spectral regions that allow for their classification, we would expect to have the same number of groups (or clusters) as the number of unique strains. The size of each group would be proportional to the number of spectra from each type of sample. The ultimate grouping of clusters (also known as the final partition) is dependent upon the method of measuring similarities (e.g. Euclidean or Pearson distances as well as the linkage method) between the spectra, and will identify groups whose observations share common characteristics. If the proper infrared regions are selected and the samples are meticulously grown and processed, the complete dendrogram will be a graphical representation of the classification of each type of bacterial strain. Therefore, to identify a particular unknown, one can analyze its infrared spectrum and subsequently determine which cluster it separates into.

Figure 5:
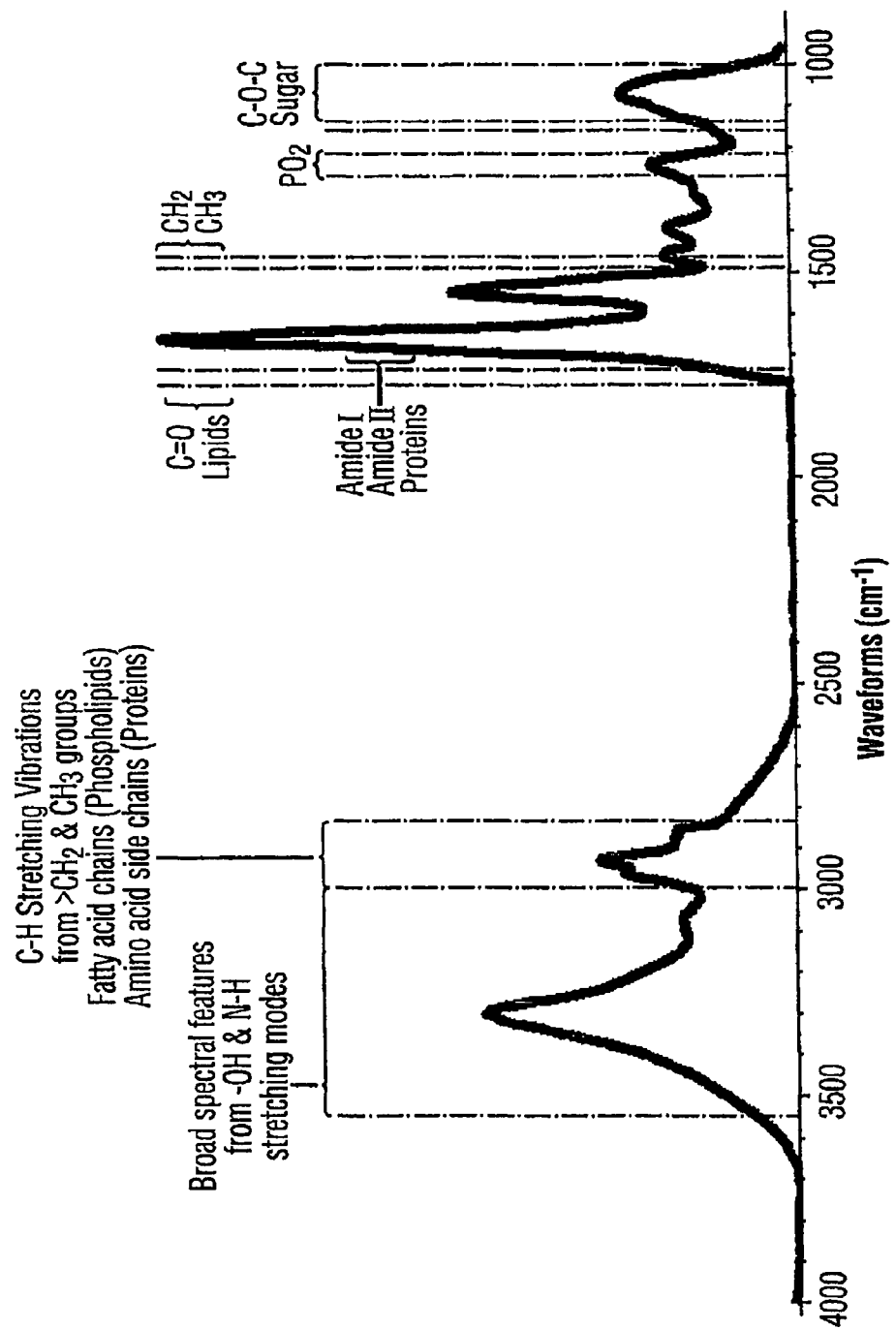
FIG. 5 is a representative IR spectrum of a bacterial cell.
Figure 6:
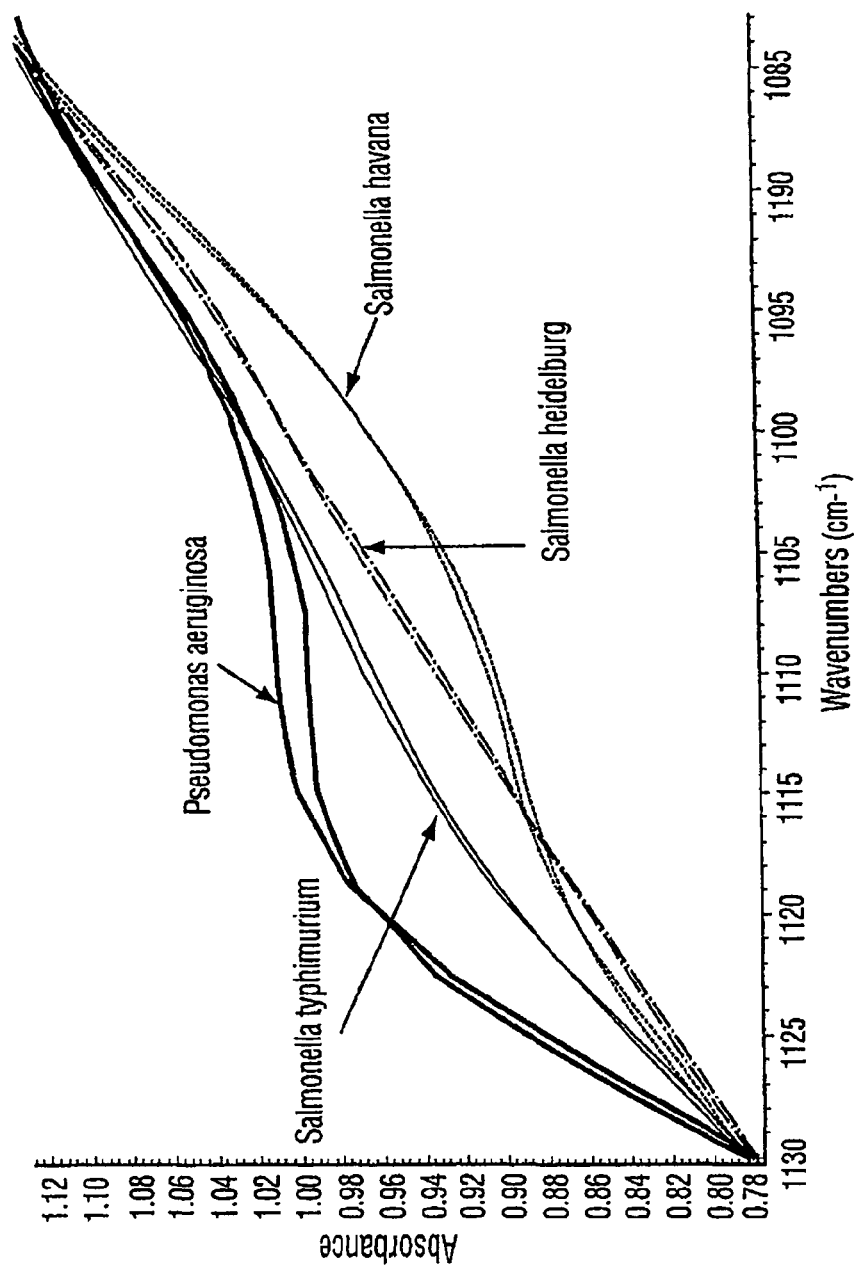
FIG. 6 shows the IR spectra of different bacteria in the 1130-1085 $cm^{-1}$ region.
Figure 7:
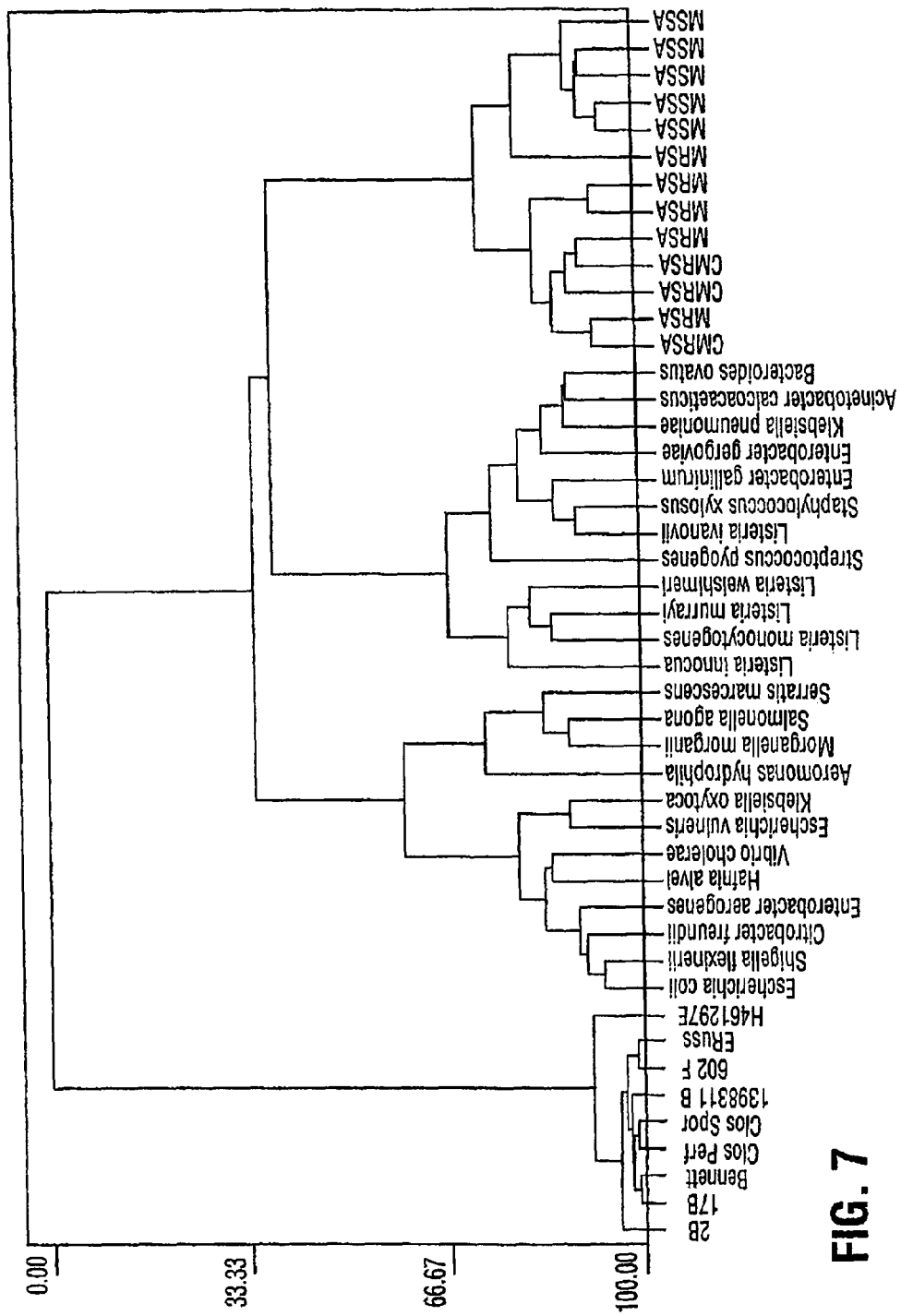
FIG. 7 is a dendrogram showing the separation of 46 bacterial samples based on the spectral region 1000 to 1530 $cm^{-1}$.

FIG. 5 shows the typical band assignment of absorption bands of bacteria. FIG. 6 shows the infrared spectra (in the region between 1130 and 1080 cm$^{-1}$) of four different bacterial samples. Subtle differences in the intensity and frequency of the absorption bands allow for the classification of each bacterial strain. FIG. 7 is a plot of a dendrogram that was generated from 46 different bacterial samples. This figure demonstrates the capability of infrared spectroscopy to distinguish between bacterial species.

Example 2

For this evaluation of FPA-FTIR spectroscopy, two Digilab Stingray systems, one equipped with a 16×16 and the other with a 32×32 array detector, were used.

Experimental Protocols

Growth of Bacteria.

Spectra of bacteria can be recorded from intact cells taken directly from culture plates. As early as the 1950s, it was recognized that the IR spectra of living bacterial cells strongly depend on the composition of the growth medium and time of growth. Consequently, extremely precise metabolic control and strict standardized handling of all samples is preferable to yield sufficient spectral reproducibility for comparison of the IR spectra of bacteria. To facilitate the use of FTIR spectroscopy in routine microbiological analysis, "Universal Medium" (UM™) was used. To date, this medium has supported the growth of virtually all bacteria and yeasts that have been tested. All 100 strain employed in the present work were grown on UM™ agar plates (provided by Quelab Laboratories Inc.) for 16 h at 37° C.

Sample Deposition.

A sterile wood toothpick was inserted into isolated colonies of bacteria to gently scrape some from the agar plate. The bacteria were then deposited onto the surface of a 38×19 mm$^2$ ZnSe crystal in ~1-mm$^2$ spots. In order to prevent cross contamination, the spots were separated by ~1-mm gaps. For each sample, 3-5 replicates were deposited. The deposited bacteria were air-dried for 10 minutes and then irradiated with ultraviolet light for a subsequent 10 minutes to sterilize the optical window.

Spectral Acquisition.

In the first study, spectra were collected on a Digilab Stingray FTS-6000 imaging spectrometer equipped with an UMA-500 infrared microscope and a 16×16 MCT FPA detector operating under Win-IR Pro 3.3. The microscope (wrapped in saran wrap) was continuously purged by dry air from a Balston dryer. For each spot of bacteria on the window, five images were collected from different locations. All images were collected by co-adding 256 scans at a resolution of 8 cm$^{-1}$ and were ratioed against a background recorded from a bare location on the optical window. Among the 256 spectra collected for each image, 3-5 were randomly selected for data analysis.

Several months later, a second study was conducted with the same system equipped with a 32×32 detector. Images were acquired from fresh cultures of the same reference strains as examined in the first study to ascertain if the spectral images of bacteria recorded with the Stingray were reproducible. Additional strains employed in this study included 31 strains isolated from different food and water sources.

Data Analysis.

The discriminatory power of FPA-FTIR spectroscopy for the differentiation of bacterial strains was evaluated through the use of hierarchical cluster analysis (HCA) using MINITAB™ software. This unsupervised approach was selected because it is based on intrinsic group structures within the spectral data. Prior to HCA, all spectra were normalized (e.g., by peak height or area) and transformed to first- or second-derivative spectra. Agglomerative clustering (i.e., beginning by combining the two most similar observations into a cluster and proceeding in this manner until all the observations form a single cluster) was performed using the Ward linkage algorithm with Euclidean distance as the metric. The spectral data from individual spectral regions containing information useful for the differentiation of bacteria were combined in various permutations to optimize the hierarchical clustering.

Results and Evaluation of Technology Potential

Figure 8:
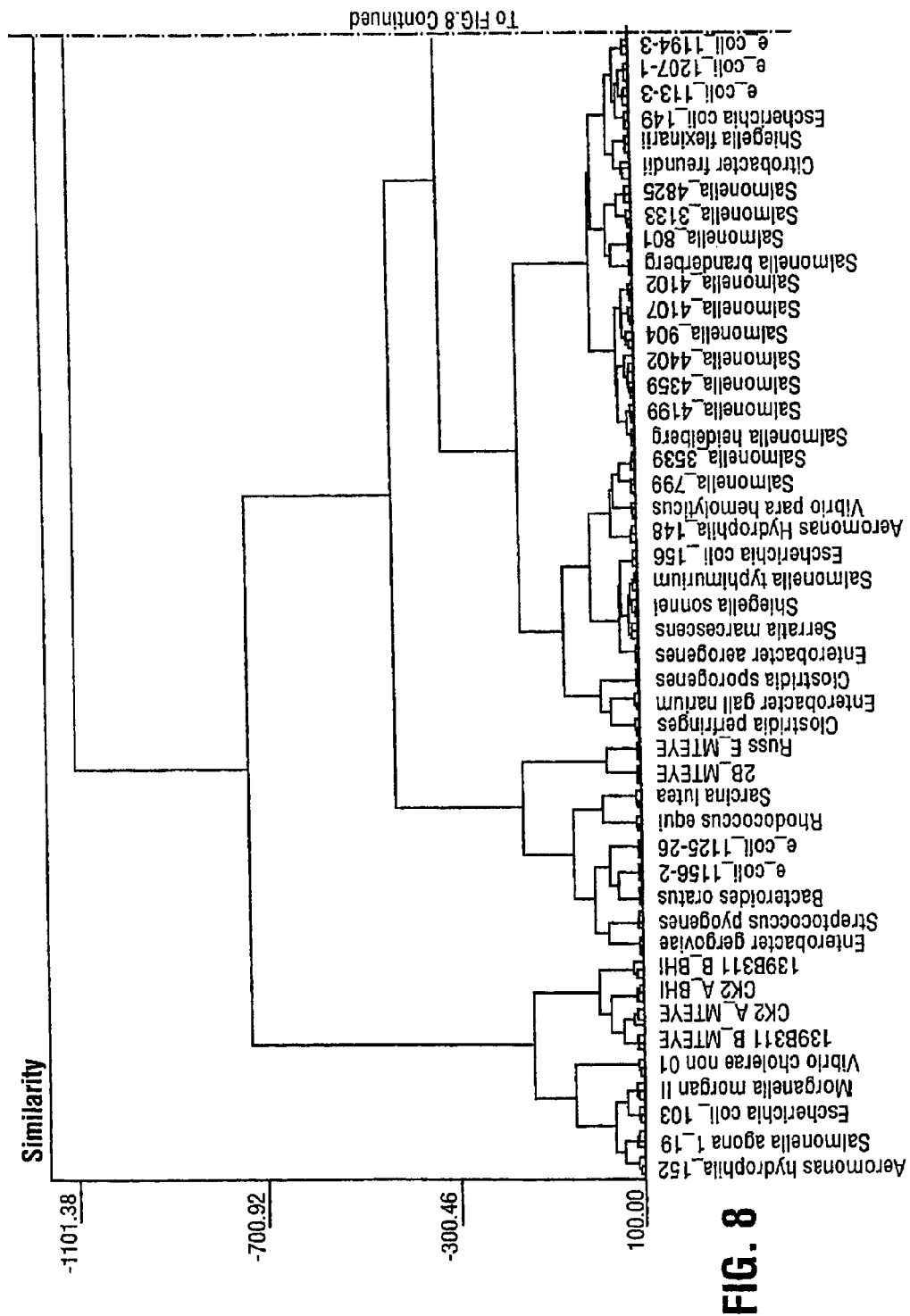
FIG. 8 is a dendrogram showing the clustering of food-borne pathogens.
Figure 9:
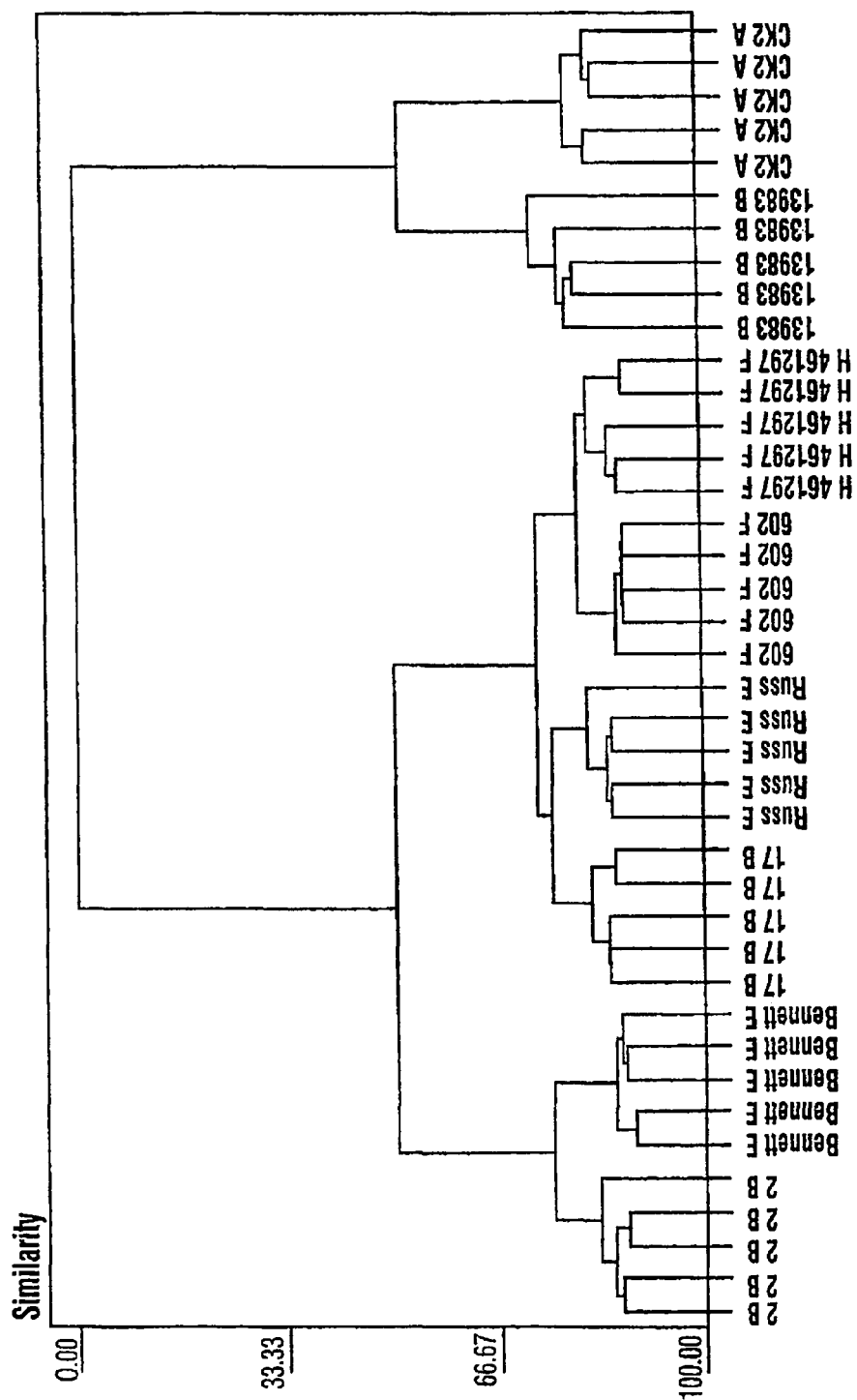
FIG. 9 is a dendrogram showing the clustering for *Clostridium botulinum* samples.
Figure 10A:
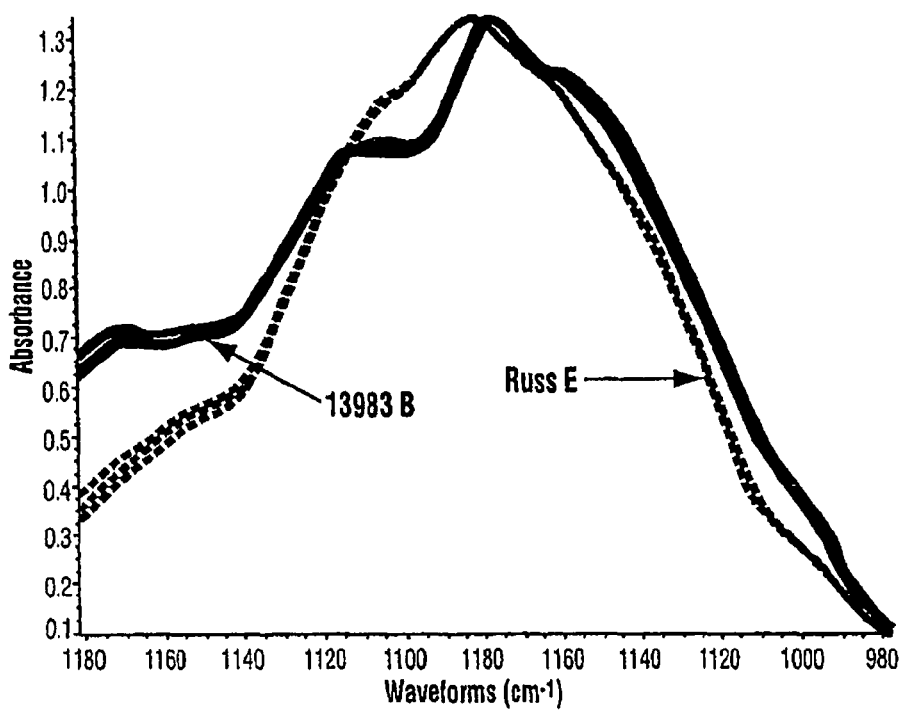
FIGS. 10 (*a*), (*b*), (*c*) and (*d*) shows spectra from *C. botillinum* strains in the spectral region: 1180 to 980 $cm^{-1}$ wherein the spectra have been baseline corrected and normalized to unit peak height.
Figure 10B:
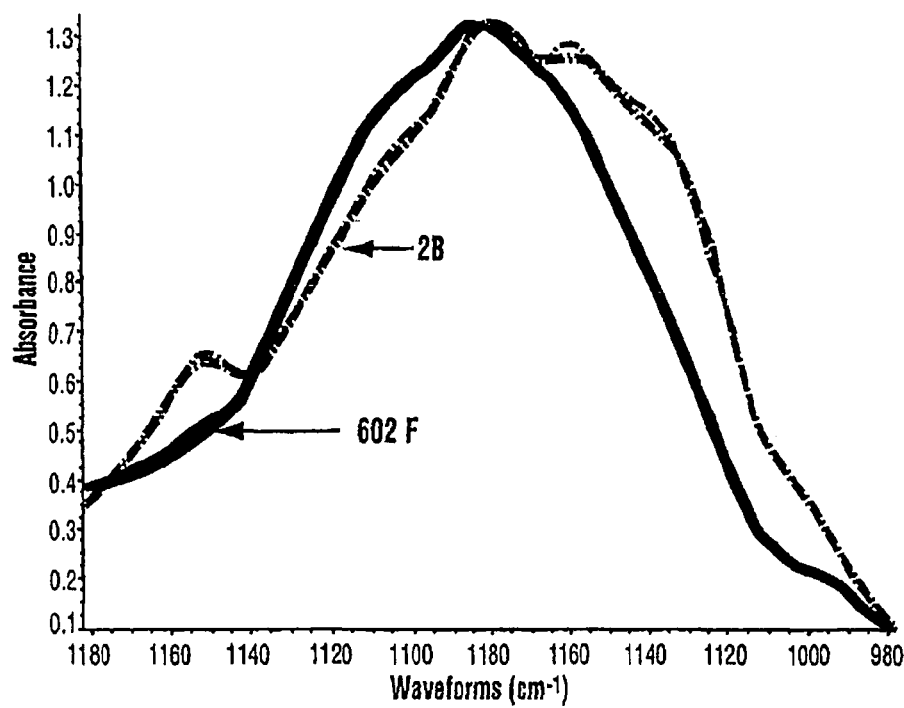
Figure 10C:
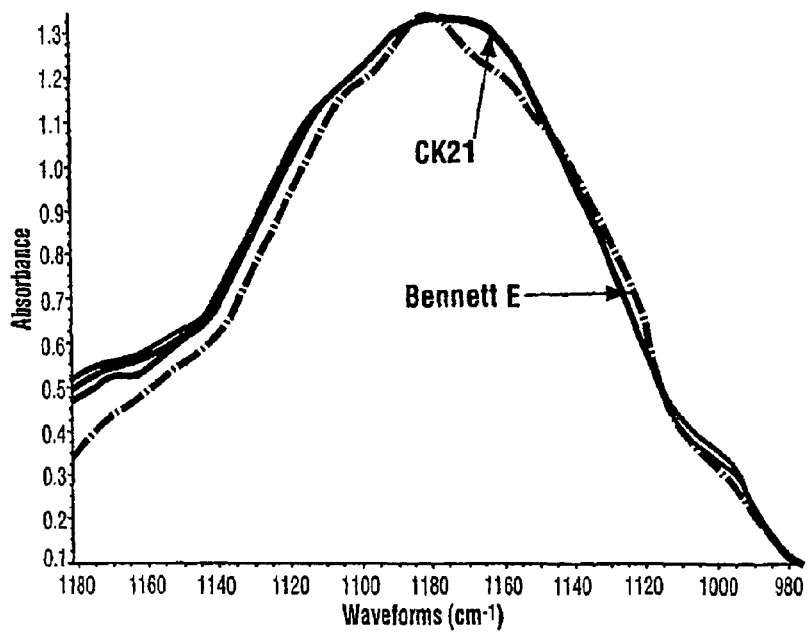
Figure 10D:
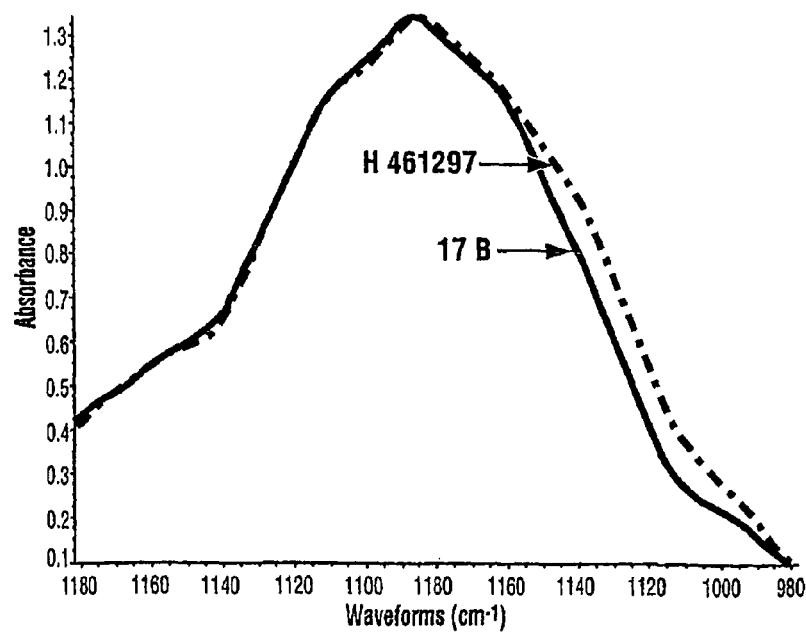

The primary objective of the experiments described above was to assess whether the Digilab FPA-FTIR system provides sufficient spectral reproducibility to meet the fundamental criterion for accurate FTIR bacteria identification, namely, that the differences among spectra of the same strain must be much smaller than differences among spectra of different strains. The bacteria analyzed comprise reference strains of most of the common foodborne pathogens as well as 31 strains isolated from different food or water sources. Evaluation of the discriminatory power of FPA-FTIR spectroscopy for the differentiation of these bacterial strains was based on inspection of dendrograms generated by HCA. A typical dendrogram obtained for samples of different genera, species, and strains is presented in FIG. 8, and a dendrogram more clearly illustrating clustering at the strain level is shown in FIG. 9. The results obtained by HCA indicated that successful discrimination among all the strains listed in Table 2 could be achieved, in that replicate spectra of the same samples were clustered together in all cases. Thus, the Euclidean distances among replicate spectra were all closer than those among spectra of different samples, fulfilling the criterion for accurate bacteria identification stated above. The results obtained with the two different array detectors employed in these studies were comparable.

Spectral reproducibility over time and between instruments was also examined in the same manner. During the first study, the spectra of selected samples were re-scanned after one week and one month, and all these samples were correctly classified by HCA, using the spectral database generated from the initially collected spectra. Attempts were also made to use this spectral database for the classification of selected samples from the second study, for which the system had been equipped with a different detector as well as a new source and optically realigned. Although these samples were all correctly classified at the genus level (e.g., *Salmonella* vs. *Listeria*), some could not be differentiated at the species level (e.g., *Listeria welshimeri* vs. *Listeria murrayi*). This is not an unusual phenomenon in FTIR bacteria identification since the spectral differences among different species of the same genus are generally smaller than those among different genera and may be very slight, thus imposing stringent requirements on spectral reproducibility.

With regard to spectral reproducibility, and hence accuracy of bacteria identification, the FPA-FTIR system has a major advantage over a conventional FTIR spectrometer, such as the FTIR bacteria analyzer, owing to the minimization of sample inhomogeneity due to the ~10$^6$-fold reduction in the size of the sample from which each spectrum is recorded. Furthermore, the homogeneity of the sample can be evaluated from the recorded image on the basis of pixel-to-pixel reproducibility and the data from any nonrepresentative portions of the sample can be rejected. Moreover, since we have found that the spectrum acquired from each pixel has sufficient SNR to allow bacteria identification, there is tremendous "built-in" redundancy in the system, further increasing the reliability of bacteria identification.

Example 3

Materials and Methods

Microbiological Specimens

A total of 8 strains of *C. botulinum* (CK2 A, 2 B, 17 B, 13983 B, Bennett E, Russ E, H461297 F, and 602 F) were used in this study. This investigation was only concerned with strains of *C. botulinum* in groups A, B, E, and F because only these serotypes give rise to intoxications in humans. The isolates were confirmed as *C. botulinum* because of the production of characteristic botulinum neurotoxins.

FTIR Spectroscopic Methods

Sample Preparation

Prior to FTIR spectral acquisition, all strains were incubated for 48 hours on both Brain Heart Infusion (BHI) and McClung Toabe with egg yolk (MTEYE) media. To optimize the growth conditions, proteolytic strains were grown at 35° C., while non-proteolytic strains were grown at 25° C. The bacteria were transferred to an infrared transmitting window (ZnSe). The bacteria were air dried on the IR window for 10 minutes and then incubated in formaldehyde vapours for several hours to ensure inactivation of botulinum neurotoxin.

FTIR Spectral Acquisition

All spectra were collected on a Digilab Stingray FTS-6000 imaging spectrometer equipped with a Digilab UMA-500 infrared microscope and a 32×32 MCT focal plane array detector (Digilab, Randolph, Mass., USA) operating under Win-IR Pro 3.3 software (Digilab). 1024 spectra were simultaneously collected from each analysis by co-adding 256 scans at a resolution of 8 $cm^{-1}$. This resulted in the acquisition of over 24,000 spectra from the eight strains of *C. botulinum*. In order to produce absorbance spectra, the raw spectra were ratioed against the spectrum from a clean portion of the IR window. A constant flow of dry air was used to purge the spectrometer and the microscope to limit spectral contributions from carbon dioxide and atmospheric water vapour.

Multivariate Data Processing

The high degree of spectral similarity of bacterial strains within the species *C. botulinum* and the fact that each spectrum contains over one thousand data points, necessitates computerized methods of classification. The primary methods of bacterial classification were principle component analysis (PCA) and hierarchical cluster analysis (HCA). The HCA results were graphically displayed through the creation of dendrograms using the software MINITAB. Dendrograms are hierarchical graphs that illustrate intrinsic group structures within complex data configurations of spectra. Prior to multivariate analysis the raw data from the spectra were normalized to unit peak height and subsequently transformed to first-derivative spectra to enhance the separation of partially superimposed IR bands and to minimize problems arising from unavoidable baseline shifts. Furthermore, the spectral ranges of interest were pre-selected to allow for proper hierarchical clustering.

Results

Spectral Feature Selection and Assignment

The eight strains exhibited significant differences in several spectral regions of the infrared spectrum. The most significant divergences occurred in the region between 1180-980 $cm^{-1}$ and as such, the data points in this range were included in the PCA and the HCA. Visual inspection of the spectra from 1180-980 $cm^{-1}$ confirmed that there were notable differences in the absorption bands of the eight *C. botulinum* strains (FIG. 10). The bands in this region arise from contributions of proteins, lipids, polysaccharides and nucleic acids that overlap to create a profile that is unique to a particular strain.

Figure 11:
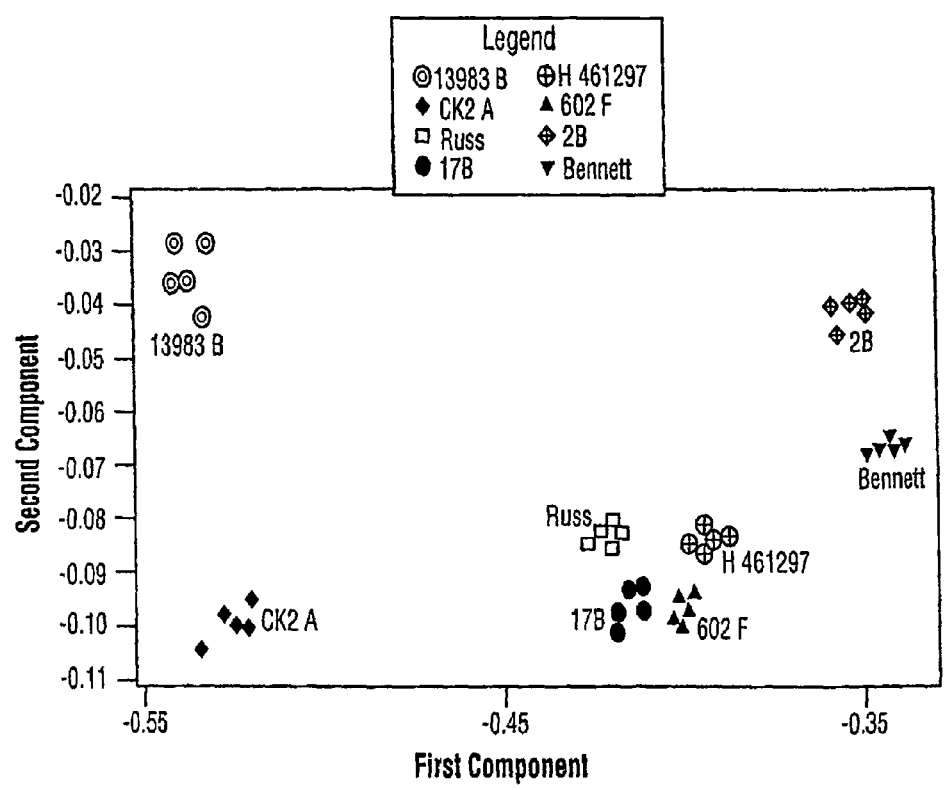
FIG. 11 shows the result of Principal Component Analysis using a commercial software in the spectral region: 1180-980 $cm^{-1}$.

Differentiation between the eight strains based on the spectral data in the region of 1180-980 $cm^{-1}$ PCA: Eight distinct clusters were observed on a score plot of PC1 vs. PC2 (FIG. 11) and were confirmed to represent complete separations of the eight strains.

Figure 12:
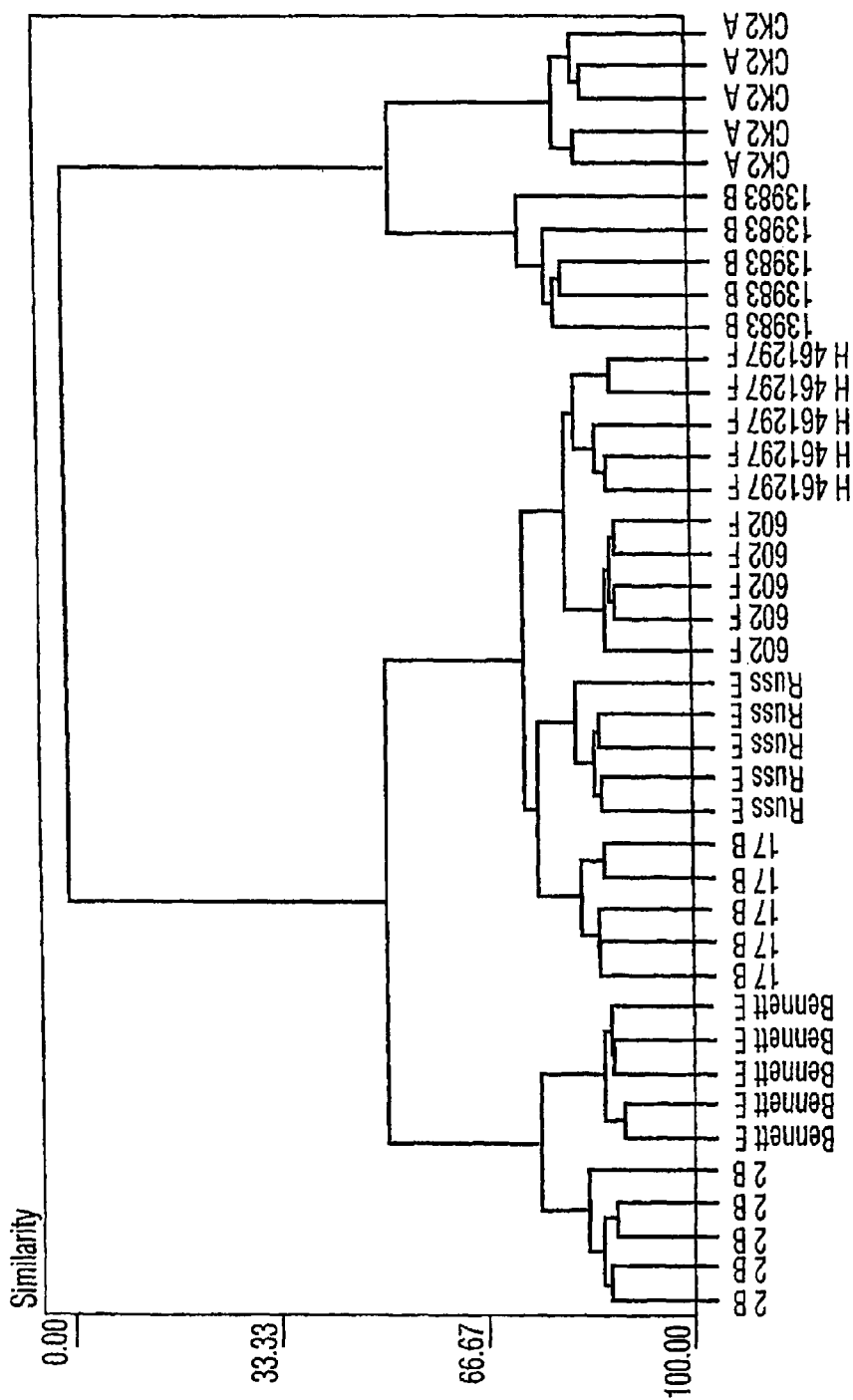
FIG. 12 is a dendrogram generated from *C. botulinum* strains in the spectral region: 1180-980 $cm^{-1}$; distance measure: Euclidean; linkage method: Complete.

HCA: Multivariate cluster analysis was used to analyze all spectra in the range of 1180-980 $cm^{-1}$. Spectral similarity was determined using the Euclidean distance and a complete linkage method (FIG. 12).

The ability to differentiate between the *Clostridium botulinum* strains by FTIR spectroscopy is dependent on appropriate processing of spectral data, meticulous sample handling and optimization of spectral ranges.

Even though there are striking visual differences in the spectra from the eight strains in the region of 1180-980 $cm^{-1}$, there is enough consistency to allow for the differentiation of proteolytic and non-proteolytic strains.

Through the systematic analysis of the IR spectra, it was determined that the eight strains of *C. botulinum* diverged most significantly in the spectral region in which characteristic absorption bands of carbohydrates are predominant. Thus, differentiation between the strains may be primarily based on structural and biochemical differences in the cell wall.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

The invention claimed is:

1. A method for characterizing a microorganism said method comprising:
    a) obtaining at least one multi-pixels spectral image of a sample of said microorganism, wherein each pixel of said multi-pixels spectral image has a corresponding spectrum;
    b) selecting one or more spectra from said multi-pixels spectral image, wherein said selecting is based on one or more spectral characteristics of said corresponding spectrum; and
    c) identifying said microorganism by comparing said one or more selected spectra with spectra of reference microorganisms from a database to determine an identity of said microorganism.

2. The method as claimed in claim 1 wherein said database is established by:
    a) obtaining at least one multi-pixels spectral image for each of a plurality of reference microorganisms samples, wherein each pixel of said multi-pixels spectral image has a corresponding spectrum; and
    b) selecting one or more spectra from said multi-pixels spectral images, wherein said selecting is based on one or more spectral characteristics, to establish said database and wherein said database comprises at least one spectrum for each of said reference microorganisms.

3. The method as claimed in claim 1, wherein said spectral characteristics are selected from: signal-to-noise, spectral intensity and spectral variability.

4. The method as claimed in claim 1, wherein said step of selecting is based on identification of a presence or absence of spectral features characteristic of chemical inhomogeneities.

5. The method as claimed in claim 1 wherein said step of selecting comprises comparing said spectral characteristics with spectral characteristics of a reference spectrum.

6. The method as claimed in claim 5 wherein said reference spectrum is an average spectrum obtained by averaging spectra of selected pixels of said multi-pixels spectral image of said reference microorganism.

7. The method as claimed in claim 6 wherein said selected pixels comprise all the pixels from said image.

8. The method as claimed in claim 1, further comprising the step of processing said selected spectra to optimize spectral comparison between spectra of said reference microorganisms and said one or more spectra of said microorganism, wherein said step of processing is selected from adjusting a baseline, obtaining a spectral derivative, normalizing peak height or intensity, smoothing, data interpolation, resolution enhancement and combination thereof.

9. The method as claimed in claim 1, wherein said database comprises at least one sub-database which comprises partial or transformed spectral data from said selected spectra to reduce dimensionality of the data space and wherein said step of comparing is performed using said at least one sub-database.

10. The method as claimed in claim 9 wherein said partial spectral data is selected based on spectral features that are characteristic of said reference microorganisms.

11. The method as claimed in claim 1, wherein said step of comparing further comprises co-adding spectra from said selected spectra to create subsets of spectra and comparing one or more of said subsets with spectra of said reference microorganism.

12. The method as claimed in claim 1, wherein said microorganisms are selected from bacteria, viruses and unicellular eukaryotes.

13. The method as claimed in claim 1 wherein said selected spectra are obtained from pre-determined pixels.

14. The method as claimed claim 1 wherein comparing is performed using a method selected from K-nearest-neighbor algorithm, artificial neural networks, multivariate statistics, support vector machines and hierarchical database distribution and combination thereof.

15. The method as claimed in claim 1 wherein said multi-pixels spectral image is obtained using a array detector.

16. The method as claimed in claim 15 wherein said array detector is selected from a linear array and a multiple arrays detector.

17. The method as claimed in claim 16 wherein the array is an infrared Focal Plane Array.

18. The method as claimed in claim 1 wherein multiple samples of microorganisms are included simultaneously in one image.

* * * * *